United States Patent [19]

Hoffman

[11] 4,429,144
[45] Jan. 31, 1984

[54] PREPARATION OF ROSE OXIDE PREDOMINANTLY CONTAINING THE Z ISOMER

[75] Inventor: Werner Hoffman, Neuhofen, Fed. Rep. of Germany

[73] Assignee: BASF Aktiengesellschaft, Ludwigshafen, Fed. Rep. of Germany

[21] Appl. No.: 448,345

[22] Filed: Dec. 9, 1982

[30] Foreign Application Priority Data

Dec. 18, 1981 [DE] Fed. Rep. of Germany ....... 3150234

[51] Int. Cl.³ .......................................... C07D 309/04
[52] U.S. Cl. .................................................. 549/356
[58] Field of Search ......................................... 549/356

[56] References Cited

U.S. PATENT DOCUMENTS

| | | | |
|---|---|---|---|
| 3,161,657 | 12/1964 | Eschenmoser et al. | 549/356 |
| 3,163,658 | 12/1964 | Eschinasi et al. | 549/356 |
| 3,166,575 | 1/1965 | Naves et al. | 549/356 |
| 3,166,576 | 1/1965 | Markus | 549/356 |
| 3,252,998 | 5/1966 | Ohloff et al. | 549/356 |
| 3,328,426 | 6/1967 | Ohloff | 549/356 |
| 3,657,278 | 4/1972 | Böse et al. | 549/356 |
| 4,340,544 | 7/1982 | Suzukamo et al. | 549/356 |

*Primary Examiner*—Nicky Chan
*Attorney, Agent, or Firm*—Oblon, Fisher, Spivak, McClelland & Maier

[57] ABSTRACT

A mixture of Z- and E-2-[2-methylprop-1-en-1-yl]-4-methyltetrahydropyran isomers, of the formulae Z-I and E-I

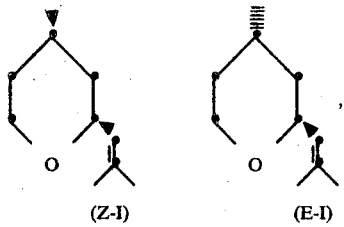

containing not less than 85% of Z-I and not more than 15% of E-I, is prepared by a process wherein 2-[2-methylprop-1-en-1-yl]-4-methylenetetrahydropyran of the formula II

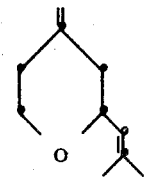

is hydrogenated over a platinum dioxide or platinum/-charcoal catalyst in the presence of a strongly acidic cation exchanger. The product is a useful fragrance material which also occurs naturally and is known as rose oxide.

1 Claim, No Drawings

PREPARATION OF ROSE OXIDE PREDOMINANTLY CONTAINING THE Z ISOMER

The present invention relates to an improved process for the preparation of a mixture of Z- and E-2-[2-methylprop-1-en-1-yl]-4-methyltetrahydropyran isomers, which are better known as Z- and E-rose oxide, the mixture containing not less than 85% of the naturally occurring Z isomer which is more useful for the perfume industry.

Since its discovery in 1960 (cf. Swiss Pat. No. 395,406), rose oxide has become increasingly important in the fragrance industry. The Z isomer has proved to be the more useful and hence the more desirable isomer. There has been no lack of attempts to prepare rose oxide, in particular a rose oxide which predominantly contains the Z isomer. In the majority of conventional processes, acyclic intermediates are used, or the pyran ring is first formed and the 2-isobutylene radical then introduced. Thus, for example, Tetrahedron Lett. 51 (1970), 4507–08 discloses that 3-methylbut-2-en-1-al may be reacted with 2-methylbut-1-en-4-ol and the product dehydrogenated to give 2-[2-methylprop-1-en-1-yl]-4-methylenetetrahydropyran (II), which may be converted by homogeneous hydrogenation in the presence of $SnCl_2/H_2PtCl_6$ to a rose oxide which principally contains the Z isomer. However, the stated process is as yet unsatisfactory for industrial use since the catalyst used for the hydrogenation is relatively expensive and is furthermore very difficult to recover because the $H_2PtCl_6$ is soluble in the product.

According to the PCT application with the international publication number WO 79/00,509, an improvement in this process comprises reducing II to rose oxide and then isomerizing the resulting isomer mixture, which still contains a high proportion of the E isomer, by treatment with an acidic agent. The reduction of II to rose oxide is carried out in this case in the presence of a Pd catalyst or Raney nickel, and the isomerization is carried out in the presence of a protic acid, eg. sulfuric acid or phosphoric acid, an acidic clay or a Lewis acid, in particular $BF_3$ in the form of its etherate. A disadvantage of this process is that the hydrogenation of II to an isomer mixture which substantially contains Z rose oxide is virtually a two-stage process in which the isomer mixture initially obtained has to be isolated by distillation before being isomerized.

It is an object of the present invention to provide a process by means of which 2-[2-methylprop-1-en-1-yl]-4-methylenetetrahydropyran (II) can be converted into rose oxide which substantially contains the Z isomer, the process being carried out in only one stage, in the presence of a catalyst system which is relatively readily obtainable and furthermore is easy to isolate from the reaction mixture and hence easy to recover.

We have found, surprisingly, that this object is achieved, and that II can be reduced in a simple manner, in one stage, to a rose oxide which contains not less than 85% of the Z isomer, if the reduction is carried out in the presence of a $PtO_2$ or Pt/C catalyst, in the presence of a strongly acidic cation exchanger.

The application accordingly relates to a process for the preparation of a mixture of Z- and E-2-[2-methylprop-1-en-1-yl]-4-methyltetrahydropyran isomers of the formulae Z-I and E-I

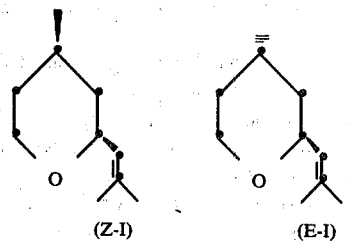

containing not less than 85% of Z-I and not more than 15% of E-I, wherein 2-[2-methylprop-1-en-1-yl]-4-methylenetetrahydropyran of the formula II

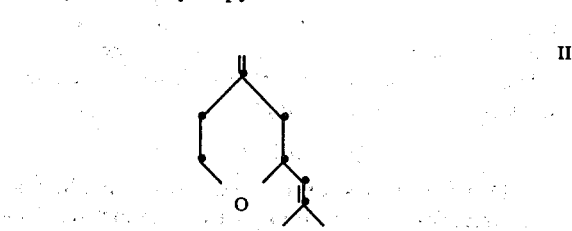

is hydrogenated over a platinum dioxide or platinum/charcoal catalyst, in the presence of a strongly acidic cation exchanger.

The catalyst employed in this reaction is a commercial $PtO_2$ catalyst or Pt/C catalyst (0.5–5% strength).

It was surprising that the process gave such good yields, since in corresponding hydrogenation reactions of II over $PtO_2$ or Pt/C catalysts in the presence of other acidic compounds either hydrogenation did not take place at all or hydrogenation occurred but not isomerization (see Comparative Examples a to f).

For the purposes of the invention, strongly acidic cation exchangers are synthetic resin ion exchangers, ie. highly polymeric three-dimensional networks of carbon atoms (matrix) which contain $SO_3^\ominus$ ions or $SO_3^\ominus$ and $O^\ominus$ ions as charge carriers (fixed ions). These are substantially commercial ion exchangers based on polystyrenesulfonic acid resins or phenolsulfonic acid resins which are known, for example, under the following tradenames: Lewatit S 100, Lewatit S 115, Lewatis SP 1080, Lewatit SC 102, Lewatit SPC 118, Amberlite IR 120, Amberlite IR 200, Amberlyst 15, Dowex 50, Permutit RS, Wofatit KPS 200, Duolite C-3, Duolite C-10, Duolite C-25, Wofatit F, Wofatit D, Wofatit P, Zeoxex (Zeokarb H), Nalcite HCR, Nalcite HGR, Nalcite HDR, Permutit Q and Permutit RS.

Regarding further details on the preparation, properties and use of the acidic cation exchangers, reference may be made to Ullmanns Encyclopadie der technischen Chemie, 3rd edition, Volume 8, 1957, page 787 et seq., and in particular pages 806–811 and 814–822.

Strongly acidic ion exchangers which furthermore are macroporous, eg. Lewatit SPC 118/H or Amberlite 200, are particularly suitable. The exchangers are employed in the dry $H^\oplus$ form.

In the batchwise procedure, in general from 0.5 to 1 g of the hydrogenation catalyst and from 10 to 100 ml of the ion exchanger are employed per mol of II. In a particular embodiment of the process, however, the hydrogenation catalyst and ion exchanger are employed as a fixed bed, substantially smaller amounts being required.

The reaction can be carried out either in the absence of a solvent or in an inert organic solvent, eg. methyl tert.-butyl ether, diethyl ether, tetrahydrofuran or cyclohexane.

The reaction is carried out in general at from 20° to 50° C., preferably at room temperature.

The hydrogen pressure during hydrogenation is in general from 0 to 1 bar above atmospheric pressure.

The dehydro-rose oxide II required as a starting material for the novel process can readily be prepared by the process described in Tetrahedron Lett. No. 51 (1970), 4507. The starting materials employed for this purpose, ie. 3-methylbut-2-en-1-al and 2-methylbut-1-en-4-ol, are commercial products.

The product can be isolated in a simple manner, by filtering off the catalyst and distilling the solution.

Both the solvent and the catalyst can be reused.

The product is a particularly useful fragrance material which also occurs naturally.

EXAMPLE 1

1,216 g (~8 moles) of a dehydro-rose oxide (about 97% strength) were taken up in 1 liter of methyl tert.-butyl ether, 1 g of PtO$_2$ and 250 ml of Lewatit SPC 118 ion exchanger in the dry H$^\oplus$ form were added, and hydrogenation was carried out at 25° C. and under a hydrogen pressure of 0.3 bar. Hydrogenation was discontinued after 192 liters of hydrogen had been absorbed, this taking about 11 hours. The progress of the reaction was monitored by gas chromatographic analyses carried out hourly. The ion exchanger and the catalyst were filtered off, the solvent was distilled off at 20° C. and under 20 mbar, and the hydrogenation product which remained was subjected to fractional distillation. 1,015 g (82% of theory) of a product of boiling point 89°–90° C./26 mbar and $n_D^{25} = 1.4536$ were obtained. According to gas chromatography, this product contained 92% of Z-rose oxide and 6.5% of E-rose oxide.

EXAMPLE 2

0.5 g of 5% strength platinum/charcoal and 50 ml of Lewatit SPC 118 ion exchanger in the dry H$^\oplus$ form were added to 152 g (1 mole) of a dehydro-rose oxide (about 97% strength), and hydrogenation was carried out at 25°–30° C. and under a hydrogen pressure of 0.3 bar. Hydrogenation was discontinued after 26 hours, during which 23.5 liters of hydrogen were absorbed. The progress of the reaction was monitored by gas chromatography. The catalyst and the ion exchanger were filtered off and washed with diethyl ether to remove adhering product, the solvent was distilled off at 50° C. and under 20 mbar, and the product which remained was fractionated over a 1 m column filled with 5 mm glass rings. 129 g (87% of theory) of product were obtained. According to gas chromatography, this product contained 90.5% of Z-rose oxide and 7% of E-rose oxide.

COMPARATIVE EXAMPLES (a) 0.5 g of 5% strength platinum/charcoal and 1 g of tin(II) chloride were added to 152 g (1 mole) of a 97% strength dehydro-rose oxide, and the mixture was stirred vigorously at 25° C., under a hydrogen atmosphere (from atmospheric pressure to 0.3 bar). No hydrogen was absorbed in the course of 24 hours.

(b) The experiment described under (a) was repeated using 1 ml of boron trifluoride etherate instead of 1 g of SnCl$_2$. In this case, also, no hydrogen was absorbed in the course of 24 hours.

(c) The experiment described under (a) was repeated using 1 g of p-toluenesulfonic acid instead of 1 g of SnCl$_2$. After 51 hours, about 24 liters of H$_2$ had been absorbed. Hydrogenation was then discontinued, the catalyst was filtered off, and the filtrate was washed neutral with NaHCO$_3$ solution and then distilled. 143 g of distillate were obtained which, according to gas chromatography and NMR analysis, contained 30% of Z-rose oxide and 52% of E-rose oxide.

(d) 0.5 g of PtO$_2$ and 2 g of SnCl$_2$ were added to 152 g (1 mole) of a dehydro-rose oxide (about 97% strength), and hydrogenation was attempted at 25°–30° C. and under a hydrogen pressure of 0.3 bar, while stirring vigorously. No hydrogen was absorbed in the course of 24 hours.

(e) The experiment described under (d) was repeated using 2 ml of boron trifluoride etherate instead of 2 g of SnCl$_2$. 24 liters of hydrogen were absorbed at 25°–30° C., in the course of 4 hours. The mixture was worked up by a procedure similar to that described in Experiment (c). Distillation gave 144 g of product which, according to gas chromatography and NMR analysis, contained 25% of Z-rose oxide and 58% of E-rose oxide.

(f) The experiment described under (d) was repeated using 2 g of p-toluenesulfonic acid instead of 2 g of SnCl$_2$. At 25°–30° C., 24 liters of hydrogen were absorbed in the course of 3 hours. Since, according to gas chromatographic analysis, the isomer ratio after this time corresponded to 31% of Z-rose oxide and 55% of E-rose oxide, the mixture was stirred for a further 24 hours at 25°–30° C. Thereafter, it was worked up as described in Experiment (c). Distillation gave 144 g of product which, according to gas chromatography, contained 32% of Z-rose oxide and 54% of E-rose oxide. Virtually no isomerization to Z-rose oxide took place.

I claim:

1. A process for the preparation of a mixture of Z- and E-2-[2-methylprop-1-en-1-yl]-4-methyltetrahydropyran isomers of the formulae Z-I and E-I

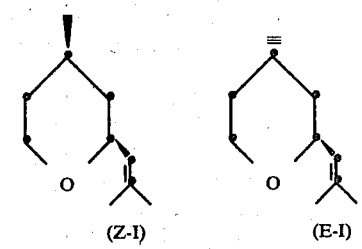

containing not less than 85% of Z-I and not more than 15% of E-I, wherein 2-[2-methylprop-1-en-1-yl]-4-methylenetetrahydropyran of the formula II

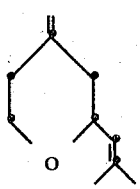

is hydrogenated over a platinum dioxide or platinum/charcoal catalyst in the presence of a strongly acidic cation exchanger.

* * * * *